United States Patent
Garcia et al.

(10) Patent No.: US 11,922,823 B2
(45) Date of Patent: Mar. 5, 2024

(54) DEMONSTRATION APPARATUS FOR A MEDICAL DEVICE AND RELATED METHOD

(71) Applicant: C.R. Bard, Inc., Tempe, AZ (US)

(72) Inventors: Edgar Sanchez Garcia, Tempe, AZ (US); Alexander William Tessmer, Phoenix, AZ (US); Andrea Bly, Tempe, AZ (US); Nicholas Loren Bajema, Phoenix, AZ (US); Matt Casiraro, Tempe, AZ (US); Mark Nicholas Wright, Tempe, AZ (US); Eric Moll, Gilbert, AZ (US); Corey Stapleton, Gilbert, AZ (US); Ricky Mori, Avondale, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 1750 days.

(21) Appl. No.: 15/414,113

(22) Filed: Jan. 24, 2017

(65) Prior Publication Data

US 2017/0213482 A1 Jul. 27, 2017

Related U.S. Application Data

(60) Provisional application No. 62/286,393, filed on Jan. 24, 2016.

(51) Int. Cl.
*G09B 23/28* (2006.01)
*A61M 25/00* (2006.01)

(52) U.S. Cl.
CPC ... *G09B 23/285* (2013.01); *A61M 2025/0008* (2013.01)

(58) Field of Classification Search
CPC .............................. G09B 23/28; G09B 23/285
See application file for complete search history.

(56) References Cited

U.S. PATENT DOCUMENTS

| | | | | | |
|---|---|---|---|---|---|
| 3,365,820 | A | * | 1/1968 | Connell | G09B 3/02 40/493 |
| 3,630,344 | A | * | 12/1971 | Bergh | A45C 11/34 220/345.2 |
| 3,766,666 | A | * | 10/1973 | Stroop | G09B 23/285 434/273 |
| 4,726,772 | A | * | 2/1988 | Amplatz | G09B 23/285 434/272 |
| 5,785,057 | A | * | 7/1998 | Fischer | A61F 5/3761 128/846 |
| 7,544,062 | B1 | * | 6/2009 | Hauschild | G09B 23/285 434/272 |

(Continued)

FOREIGN PATENT DOCUMENTS

WO 2015153599 A1 10/2015

*Primary Examiner* — Eugene L Kim
*Assistant Examiner* — Alyssa M Hylinski
(74) *Attorney, Agent, or Firm* — Dickinson Wright PLLC; Andrew D. Dorisio

(57) ABSTRACT

An apparatus for demonstrating the use of a medical device includes a body adapted for receiving the medical device. The body includes at least a portion adapted for viewing the medical device when positioned in the body. A cover is provided for selectively covering the portion of the body adapted for viewing the medical device. A kit and related methods are also disclosed.

7 Claims, 4 Drawing Sheets

(56) References Cited

U.S. PATENT DOCUMENTS

Figure 1:
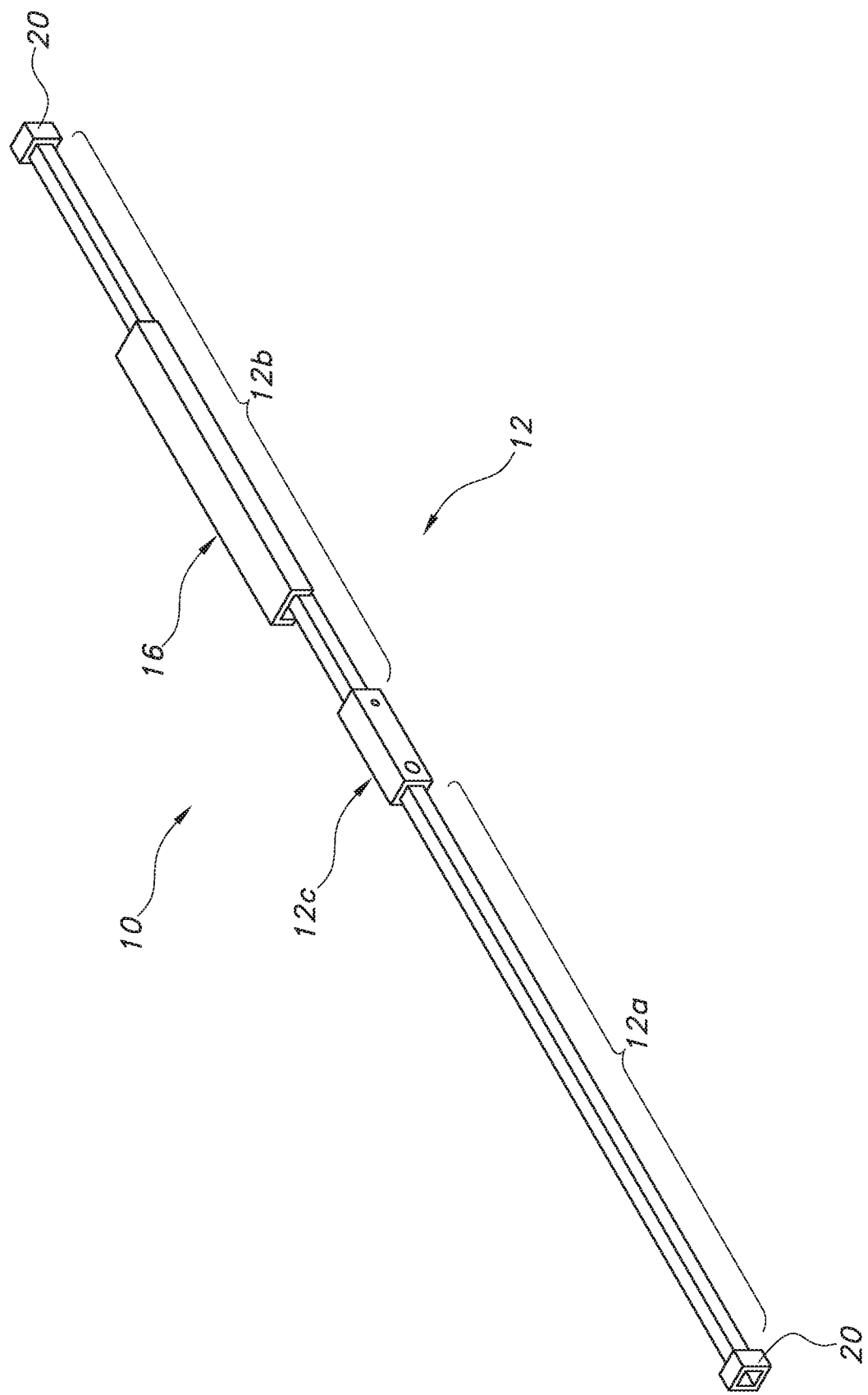

| | | | | |
|---|---|---|---|---|
| 7,648,367 | B1* | 1/2010 | Makower | G09B 23/285 |
| | | | | 434/262 |
| 8,439,687 | B1* | 5/2013 | Morriss | G09B 23/285 |
| | | | | 434/267 |
| 8,480,400 | B1* | 7/2013 | Armbruster | G09B 17/02 |
| | | | | 434/181 |
| 9,275,556 | B1* | 3/2016 | East | G09B 23/285 |
| 2004/0256581 | A1* | 12/2004 | Au | A61L 2/10 |
| | | | | 250/504 H |
| 2005/0113764 | A1* | 5/2005 | Watkins | A61M 5/3243 |
| | | | | 604/197 |
| 2012/0164616 | A1* | 6/2012 | Endo | A61B 1/00057 |
| | | | | 434/267 |
| 2014/0271400 | A1* | 9/2014 | Cheng | B01L 3/5023 |
| | | | | 422/417 |
| 2014/0370474 | A1* | 12/2014 | Thompson | A61B 1/00131 |
| | | | | 434/262 |
| 2016/0217707 | A1* | 7/2016 | Jutila | A61F 6/18 |
| 2017/0061830 | A1* | 3/2017 | Kogiso | G09B 23/30 |
| 2017/0294143 | A1* | 10/2017 | Long, Jr. | G09B 23/285 |

\* cited by examiner

DEMONSTRATION APPARATUS FOR A MEDICAL DEVICE AND RELATED METHOD

This application claims the benefit of U.S. Provisional Patent Application Ser. No. 62/286,393, the disclosure of which is incorporated herein by reference.

TECHNICAL FIELD

This disclosure relates to the medical device arts and, in particular, to an apparatus for demonstrating the proper use of a medical device, such as to clinicians in need of training.

BACKGROUND

A clinician performing an endovascular procedure, such as angioplasty, will typically use fluoroscopy in the course of performing a diagnostic angiogram to assess the location of an area for providing a treatment (such as where a lesion or blockage is present in the vasculature). Upon gaining guidewire access to the vasculature using additional fluoroscopy, and then inserting the catheter along the guidewire, the clinician will then typically use even more fluoroscopy, either continuously or intermittently (e.g., "spot checking"), in order to confirm the catheter has reached the location for treatment. As can be appreciated, this conventional approach increases the exposure of the patient and others, including the clinician and assistants, to fluoroscopy and, hence, radiation, which is generally desired to be avoided to the greatest extent possible.

In an effort to address this issue, the present applicant has proposed a technology in which external markings on the catheter are used to ensure that the catheter has reached the target area for treatment, which may be determined during a pre-dilatation step. This may avoid the need for the continuous use of fluoroscopy during the procedure, since the clinician is assured by viewing the marking relative to a fixed location that the target area is reached prior to commencing the treatment (such as the inflation of a balloon or activation of another device associated with the catheter). However, since this approach is not conventional, there is a need to demonstrate the efficacy of the technology outside of the patient, and also for proper training in the new technique.

Accordingly, a need is identified for a relatively simple and inexpensive apparatus for demonstrating the use of a medical device.

SUMMARY

According to one aspect of the disclosure, an apparatus for demonstrating the use of a medical device is proposed. The apparatus may include a body adapted for receiving the medical device. The body includes at least a portion adapted for viewing the medical device when positioned in the body, and a cover for selectively covering the portion of the body adapted for viewing the medical device.

In one particular arrangement, the medical device is a catheter with external markings for denoting the position of the catheter within the patient (such as the distance of insertion), which markings can this be used to position the catheter at a target location for treatment without the continuous or constant use of fluoroscopy to confirm that the target location has been reached. In such case, the apparatus is especially adapted for demonstrating to the clinician the ability to ensure the device has reached the treatment location without the use of fluoroscopy.

According to a further aspect of the disclosure, a method of demonstrating the use of a medical device including a marking is disclosed. The method comprises at least partially inserting the medical device into a body to a simulated treatment location, such that the medical device at the simulated treatment location is visible to a clinician or other person being trained. The method further comprises observing a position of the marking external to the body. The method also comprises moving the medical device relative to the body so that the marking does not correspond to the position, then returning the medical device so that the marking corresponds to the position. In one embodiment, the method includes obscuring the simulated treatment location from view after the observing step, and revealing the simulated treatment location after the moving step.

Still a further aspect of the disclosure pertains to a kit comprising a catheter in combination with a vessel including an indicia identifying a simulated treatment location. The kit may include a catheter with a marking for identifying a distance between the marking and a distal portion of the catheter, and the simulated vessel includes a transparent wall adjacent to the indicia for viewing the distal portion of the catheter when the marking is positioned at a predetermined location. A cover may also be provided for at least partially covering the transparent wall, along with a body for supporting the vessel. The body may comprise a distal portion coupled to a proximal portion by a coupler.

A further aspect of the disclosure pertains to a method of simulating the use of a medical device. The method comprises providing a first simulation of the medical device under fluoroscopy, and providing a second simulation of the medical device without fluoroscopy. The step of providing the first simulation may comprise uncovering a transparent vessel including the medical device. The step of providing the second simulation may comprise the step of providing the second simulation comprises covering the transparent vessel including the medical device.

BRIEF DESCRIPTION OF THE DRAWING FIGURES

Figure 2:
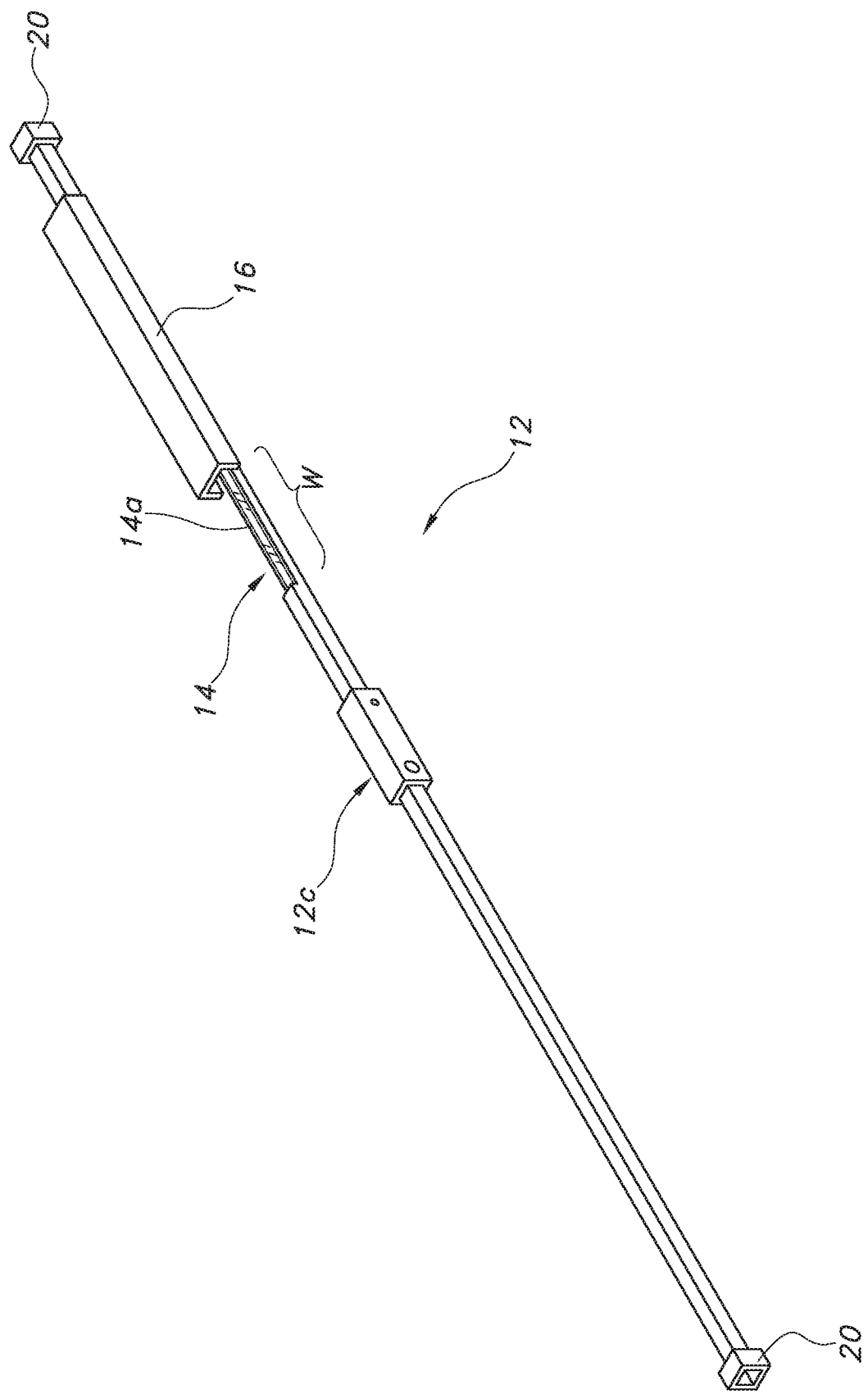
Figure 3:
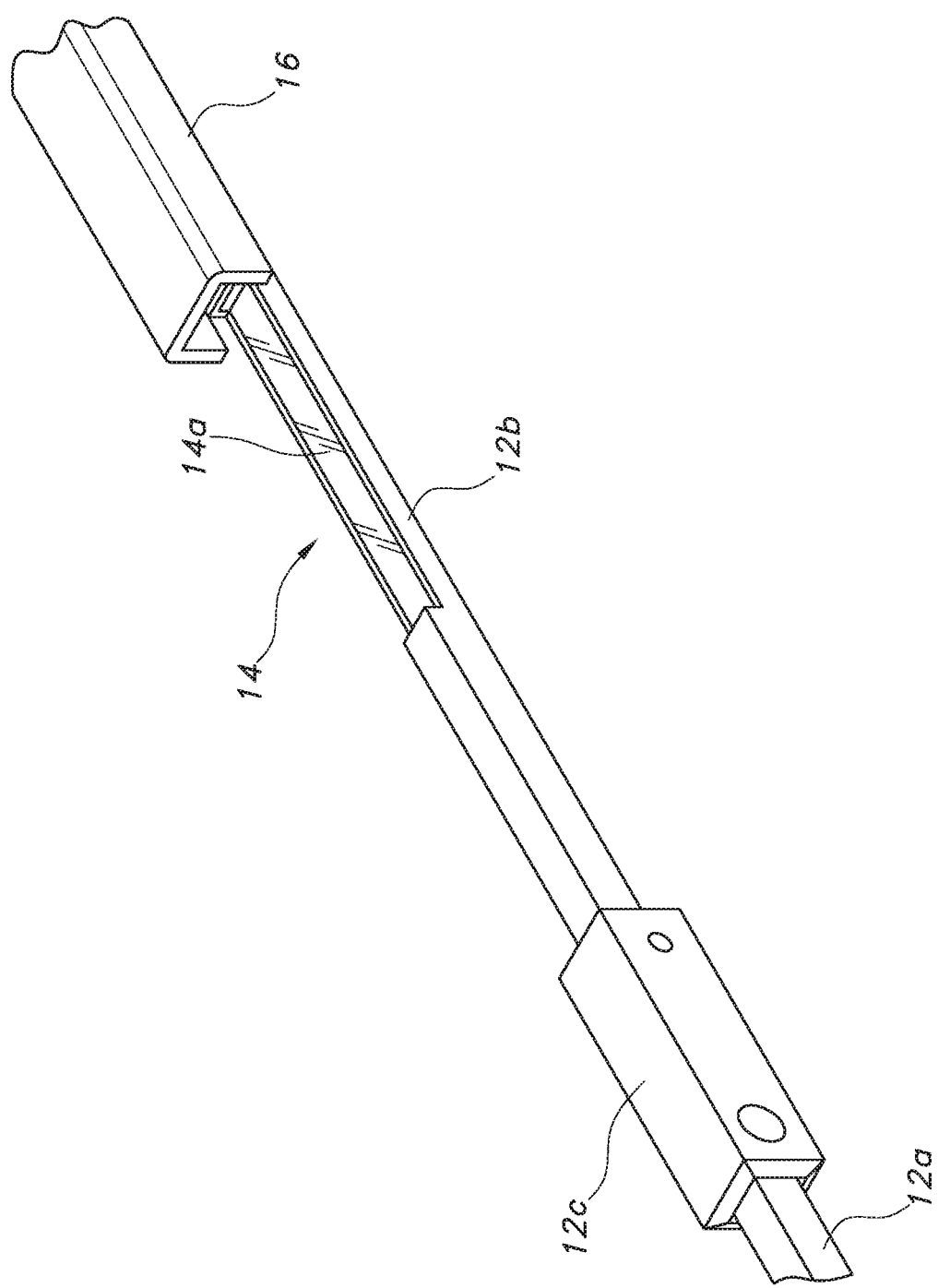
Figure 4:
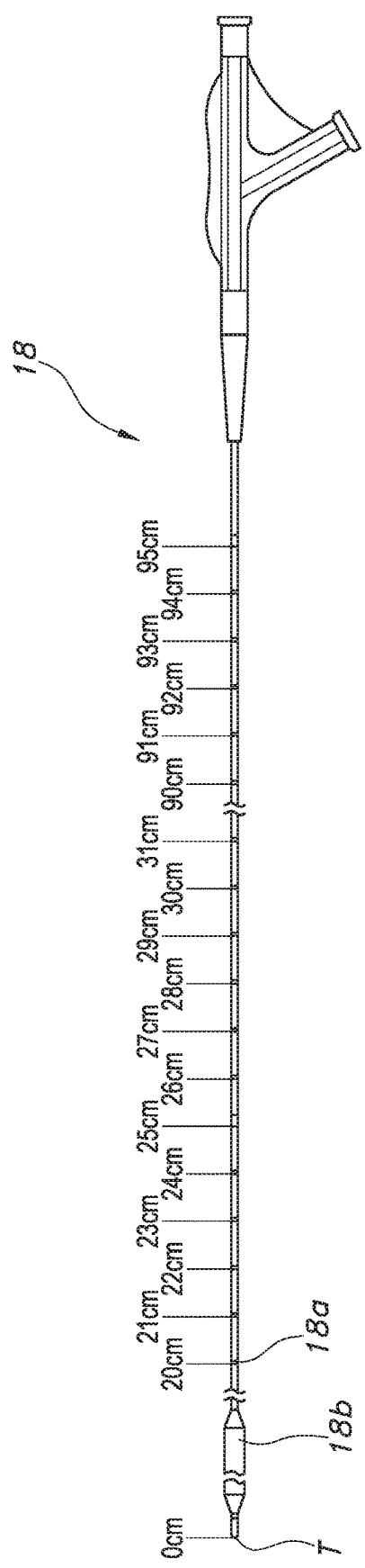

The accompanying drawing figures incorporated herein and forming a part of the specification, illustrate several aspects of a demonstration apparatus and, together with the description, serve to explain certain principles thereof. In the drawing figures:

FIGS. 1, 2 and 3 are different views of the demonstration apparatus; and FIG. 4 is a view of a medical device in the form of a balloon catheter for use in connection with the demonstration apparatus.

Reference will now be made in detail to the presently disclosed embodiments of the inventive aspects of the demonstration apparatus, examples of which are illustrated in the accompanying drawing figures.

DETAILED DESCRIPTION

With reference to FIG. 1, a possible embodiment of a demonstration apparatus 10 forming one aspect of this disclosure is illustrated. The apparatus in this embodiment includes a body 12 having a proximal portion 12a and a distal portion 12b. The body 12 may be elongated.

To allow for the apparatus to be reduced in size for storage or transport prior to use, or made "portable," the proximal and distal portions 12a, 12b of the body 12 may be releasably coupled together, such as by a magnetic coupling 12c

(e.g., a receiver including magnets for forming connections with the proximal and distal portions 12a, 12b, which may comprise a lightweight metal, such as aluminum alloys that exhibit sufficient magnetism to form a coupling, stainless steel or the like). While a magnetic coupling is preferred for ease of use, other forms of couplings may also be used, such as a threaded connection, bayonet fitting, or the like. The particular form is not considered important, as long as the portions 12a, 12b are held together in a reliable manner.

The body 12 may be hollow or tubular, and may be adapted for receiving a medical device, such as a catheter (see FIG. 4). As perhaps best understood from FIGS. 2 and 3, the distal portion 12b of the body 12 includes a window W, which allows for a user of the apparatus 10 to view the medical device when passed into the passage in the tubular body 12. A cover 16 is also provided for selectively covering the window W, and may be mounted for sliding over and along the distal portion 12b of the body 12. The cover 16 may comprise a tubular structure having a length that is substantially less than the length of either the proximal or distal portions 12a, 12b.

In one particular embodiment, the body 12 further includes an internal vessel, such as a transparent plastic tube 14 (which may be made of a durable material, such as polycarbonate). The tube 14 may be adapted to extend at least along the window W of the distal portion 12b of the body 12. The tube 14 may include a simulated treatment location 14a, such as a marking or plurality of markings simulating the existence of a lesion in the vessel (which as can be appreciated may be representative of a blood vessel or similar lumen in a body).

In one exemplary application, the apparatus 10 may be used to demonstrate to clinicians the proper use and efficacy of a medical device, such as a balloon catheter 18, as shown in FIG. 4. As can be understood, this catheter 18 may include one or more markings 18a, which are indicators normally viewable by the clinician outside of the vasculature to indicate the position of a distal portion of the catheter 18 (such as including an inflatable balloon 18b) relative to a targeted area for treatment. Specifically, as shown in FIG. 4, the markings 18a may include an indication of a distance to a pre-determined location on the catheter 18 (such as, for example, the distal tip T, a center of a working surface of the balloon 18b, or any other desired location). This may allow the clinician to reach the target area without the use of fluoroscopy, since the marking indicates that the proper location has been reached (which may be determined during a pre-dilatation interventional procedure).

Thus, using the apparatus 10 (and without involving any patient or surgical procedure), the catheter 18 may be inserted such that a distal portion thereof (including, for example, the balloon) is positioned in alignment with the window W and the simulated treatment location 14a of the vessel when the vessel 14 is present. For this step, the cover 16, if present, would be withdrawn such that the window W is fully visible. This visibility may be considered representative of the visibility of the balloon 18b relative to the target location in the vasculature under fluoroscopy (but, again, though, the apparatus 10 is merely providing a simulation).

With the catheter 18 properly positioned, the location of the marking 18a relative to an end of the proximal portion 12a may be noted (which end may include a tubular cap 20 for insertion therein to ensure that a smooth, identifiable edge is provided, and a similar cap may also be provided at the end of the distal portion 12b, as shown). The catheter 18 may then be moved or withdrawn, such that the balloon 18b no longer corresponds to the simulated treatment location 14a. The cover 16 may then be moved over the window W to obscure it (these steps can be performed in any order).

The catheter 18 (or a different device with similar markings, such as for example a different type of catheter) may then be re-inserted into the body 12 to a position at which the marking 18a corresponds to the end of the proximal portion 12a. With the cover 16 still in position, an observer would be unsure as to whether the balloon 18b is positioned at the simulated treatment location 14a, which is thus representative of the lack of using fluoroscopy to re-position the catheter 18. The cover 16 may then be moved (such as by sliding) to reveal the window W, and illustrate that the balloon 18b is located at the simulated treatment location 14a, in the exact same location as was established during the initial positioning with the cover 16 removed to expose the window W.

As can be appreciated, the apparatus 10 thus in a simple and inexpensive manner allows for the demonstration of a medical device, such as the balloon catheter of FIG. 4. The apparatus 10 can thus be demonstrated to illustrate the efficacy of the procedure involving the device without the need for actually inserting the device into the vasculature. Similarly, the apparatus 10 may be used to train clinicians or others in the proper use of the device, again without any risk to a patient or being exposed to fluoroscopy (despite the simulation thereof by use of the selective covering of the window W).

While the medical device is shown as a catheter 18 with a balloon 18b, is should be appreciated that the apparatus 10 could be used in connection with other devices for insertion into lumens, without limitation. The apparatus 10 may also be used in connection with an introducer (not shown) for enhancing the simulation, which may be positioned adjacent to the end cap 20 at the end of the proximal portion 12a.

The foregoing descriptions of one possible embodiment of a training apparatus and related methods provide illustration of the inventive concepts. The descriptions are not intended to be exhaustive or to limit the disclosed invention to the precise form disclosed. For instance, a transparent vessel or tube 14 is optional, and the treatment location could be indicated at the edges of the window W. Modifications or variations are also possible in light of the above teachings. For instance, the markings 18a are shown as indicia and numbers, but could comprise letters, symbols, colors, dimples, depressions, or any other perceptible indicators. Also, "transparent" is meant to mean any condition whereby the medical device may be visible though the wall of the tube 14, and thus may encompass some degree of translucence. Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. The term "comprising" is not meant to be limiting. The above-described configurations, elements or complete assemblies and methods and their elements for carrying out the invention, and variations of aspects of the invention can be combined and modified with each other in any combination.

The invention claimed is:
1. An apparatus for demonstrating the use of a medical device, comprising:

a hollow tubular body including an internal passage having an open end adapted for receiving the medical device, the body including a first side including at least a portion comprising a window for viewing the medical device when positioned in the body and a portion that does not comprise a window; and a cover for selectively covering and obscuring from view the window, the cover movable along the body between a position for covering the window and a position for uncovering the window;

wherein the window includes an indicia indicating a simulated treatment location.

2. The apparatus of claim 1, wherein the window is transparent.

3. The apparatus of claim 1, wherein the cover is opaque.

4. The apparatus of claim 1, wherein the portion comprises an opening.

5. The apparatus of claim 1, wherein the body comprises a transparent tube.

6. An apparatus for demonstrating the use of a medical device, comprising:

an at least partially transparent vessel having an open end portion; and a cover for selectively covering and uncovering the at least partially transparent vessel for viewing the medical device when positioned in the transparent vessel;

wherein the at least partially transparent vessel is adapted for receiving the medical device without removing the cover therefrom;

a tubular body in which the at least partially transparent vessel is located, the tubular body comprising a window.

7. An apparatus for demonstrating the use of a medical device, comprising:

an at least partially transparent vessel having an open end portion; and a cover for selectively covering and uncovering the at least partially transparent vessel for viewing the medical device when positioned in the transparent vessel;

wherein the at least partially transparent vessel is adapted for receiving the medical device without removing the cover therefrom;

a tubular body in which the at least partially transparent vessel is located, wherein the cover is slidably mounted to the tubular body.

\* \* \* \* \*